United States Patent [19]
Windle et al.

[11] Patent Number: 5,856,096
[45] Date of Patent: Jan. 5, 1999

[54] RAPID AND SENSITIVE ASSAYS FOR DETECTING AND DISTINGUISHING BETWEEN PROCESSIVE AND NON-PROCESSIVE TELOMERASE ACTIVITIES

[75] Inventors: Bradford E. Windle; Ming Qiu; Shih-Fong Chen; Terace M. Fletcher; Ira Maine, all of San Antonio, Tex.

[73] Assignee: CTRC Research Foundation, San Antonio, Tex.

[21] Appl. No.: 531,743

[22] Filed: Sep. 21, 1995

[51] Int. Cl.[6] .............................. C12Q 1/68; C12P 19/34; C07H 21/04; C12N 9/00
[52] U.S. Cl. .......................... 435/6; 435/91.2; 435/91.1; 435/174; 536/24.3; 536/24.33
[58] Field of Search .............................. 435/6, 91.2, 91.1, 435/174; 536/300, 24.3, 0.33

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 4,800,159 | 1/1989 | Mullis et al. . |
| 4,883,750 | 11/1989 | Whiteley et al. ............................ 435/6 |
| 4,957,858 | 9/1990 | Chu et al. . |
| 4,988,617 | 1/1991 | Landegran et al. ......................... 435/6 |
| 5,091,302 | 2/1992 | Newman et al. ............................ 435/6 |
| 5,268,301 | 12/1993 | Potter ....................................... 436/57 |
| 5,364,760 | 11/1994 | Chu et al. . |
| 5,403,711 | 4/1995 | Walder et al. . |
| 5,484,701 | 1/1996 | Cocuzza et al. ............................ 435/6 |

FOREIGN PATENT DOCUMENTS

| | | |
|---|---|---|
| 0 329 822 B1 | 6/1994 | European Pat. Off. . |
| 2 202 328 | 9/1988 | United Kingdom . |
| 2 202 328 | 7/1991 | United Kingdom . |
| WO 95/13381 | 5/1995 | WIPO . |
| WO 95/13382 | 5/1995 | WIPO . |
| WO 95/13383 | 5/1995 | WIPO . |

OTHER PUBLICATIONS

Lee et al. Molecular and Cellular Biology 13; 6586–6599, 1993.
Portsmann et al. J. of Virological Methods 31:181–188, 1991.
Schwartz, Bioscience Reports 1:387–398, 1981.
Autexeier and Greider:Genes and Development 9:2227–2239 (of interest), 1995.
Prowse PNAS 90:1493–1497, 1993.
Brodeur, "Do the ends justify the means?," *Nature Medicine*, 1(1):203–205, Mar., 1995.
Chadeneau et al., "Telomerase Activity Associated with Acquisition of Malignancy in Human Colorectal Cancer," *Cancer Research*, 55:2533–2536, Jun., 1995.
Chen et al., "Effect of 3'-azidothymidine triphosphate (AZTTP) and 3'-azidothymidine (AZT) on telomerase activity and telomere function," *Abstract*, Proceedings of the American Association for Cancer Research, 36:554, Mar., 1995.

Counter et al., "Telomerase activity in human ovarian carcinoma," *Proc. Natl. Acad. Sci. USA*, 91:2900–2904, Apr., 1994.
Counter et al., "Stabilization of Short Telomeres and Telomerase Activity Accompany Immortalization of Epstein–Barr Virus–Transformed Human B Lymphocytes," *Journal of Virology*, 68(5):3410–3414, May, 1994.
Counter et al., "Telomere shortening associated with chromosome instability is arrested in immortal cells which express telomerase activity," *The EMBO Journal*, 11(5):1921–1929, 1992.
Hastie et al., "Telomere reduction in human colorectal carcinoma and with ageing," *Nature*, 346:866–868, Aug., 1990.
Hiyama et al., "Telomerase Activity in Small–Cell and Non–Small–Cell Lung Cancers," *Journal of the National Cancer Institute*, 87(12):895–902, Jun., 1995.
Hiyama et al., "Correlating telomerase activity levels with human neuroblastoma outcomes," *Nature Medicine*, 1(3):249–255, Mar., 1995.
Hiyama et al., "Alterations in telomeric repeat length in lung cancer are associated with loss of heterozygosity in p53 and Rb," *Oncogene*, 10:937–944, 1995.
Hiyama et al., "Length of Telomeric Repeats in Neuroblastoma: Correlation with Prognosis and Other Biological Characteristics," *Jpn. J. Cancer Res.*, 83:159–164, Feb., 1992.
Kim et al., "Specific Association of Human Telomerase Activity with Immortal Cells and Cancer," *Science*, 266:2011–2015, Dec., 1994.
Maine et al., "In vitro investigations of processive and non–processive telomerase activities," *Abstract*, Proceedings of the American Association for Cancer Research, 36:554, Mar., 1995.
McEachern et al., "The Yeast Kluyveromyces Lactis as a Model System to Study Telomere Length Regulation and the Ability of Cells to Grow in the Absence of Telomerase," *Abstract*, Proceedings of The American Association for Cancer Research, 36:670–674, Mar., 1995.
Morin, "Is Telomerase a Universal Cancer Target?," *Journal of the National Cancer Institute*, 87(12):859–861, Jun., 1995.
Morin, "The Human Telomere Terminal Transferase Enzyme is a Ribonucleotide That Synthesizes TTAGGG Repeats," *Cell*, 59:521–529, Nov., 1989.

(List continued on next page.)

*Primary Examiner*—W. Gary Jones
*Assistant Examiner*—Dianne Rees
*Attorney, Agent, or Firm*—Arnold, White & Durkee

[57] ABSTRACT

Improved telomerase activity assays are provided in which a ligation sequential reaction (LSR) or BrdUTP are used to identify a telomerase specific product. These assays are useful in diagnosing various cancers and determining the clinical prospects for cancer patients. In addition, the assays can be used to screen for substances that interfere with telomerase activity.

42 Claims, 9 Drawing Sheets

OTHER PUBLICATIONS

Moyzis et al., "A highly conservative repetitive DNA sequence, (TTAGGG)$_n$, present at the telomeres of human chromosomes," *Proc. Natl. Acad. Sci. USA*, 85:6622–6626, Sep., 1988.

Nilsson et al., "Telomerase activity in vivo in human malignant hematopoietic cells," *Oncogene*, 9:3043–3048, 1994.

Ohara et al., "One–sided polymerase chain reaction: The amplification of cDNA," *Proc. Natl. Acad. Sci. USA*, 86:5673–5677, Aug., 1989.

Ohyashiki et al., "Telomere Shortening Associated with Disease Evolution Patterns in Myelodysplastic Syndromes," *Cancer Research*, 54:1557–1560, Jul., 1994.

Prowse et al., "Identification of a nonprocessive telomerase activity from mouse cells," *Proc. Natl. Acad. Sci. USA*, 90:1493–1497, Feb., 1993.

Rhyu, "Telomeres, Telomerase, and Immortality," *Journal of the National Cancer Institute*, 87(12):884–894, Jun., 1995.

Walker et al., "Isothermal in vitro amplification of DNA by a restriction enzyme/DNA polymerase stem," *Proc. Natl. Acad. Sci. USA*, 89:392–396, Jan., 1992.

Windle et al., "Nucleotide specificity and inhibition on telomerase, and cellular resistance to telomerase inhibition," *Abstract*, Proceedings of the American Association for Cancer Research, 36:556, Mar., 1995.

RAPID AND SENSITIVE ASSAYS FOR DETECTING AND DISTINGUISHING BETWEEN PROCESSIVE AND NON-PROCESSIVE TELOMERASE ACTIVITIES

BACKGROUND OF THE INVENTION

I. Field of the Invention

The present invention relates to the field of cancer biology. More specifically, the present invention provides methods for the diagnosis of cancer and for the screening of substances that can be used to treat cancer. A particular embodiment of the present invention involves an assay for the detection of telomerase activity in a patient tissue sample.

II. Related Art

Cancers are one of the leading causes of mortality in the world, being responsible for over one-half million deaths in the United States each year. Prompt clinical intervention is important in lowering the mortality rate and, therefore, it is important to provide improved methods for detecting cancers, especially at relative early stages.

One of the new areas of interest in tumor biology relates to the role of telomeres in cellular growth control. Telomeres are repeated sequences found at chromosome ends and it has long been known that chromosomes with truncated ends are unstable, tend to fuse with other chromosomes and are otherwise lost during cell division. Some data suggest that telomeres interaction the nucleoprotein complex and the nuclear matrix. One putative role for telomeres includes stabilizing chromosomes and shielding the ends from degradative enzyme.

Another possible role for telomeres is in replication. According to present doctrine, replication of DNA requires starts from short RNA primers annealed to the 3'-end of the template. The result of this mechanism is an "end replication problem" in which the region corresponding to the RNA primer is not replicated. Over many cell divisions, this will result in the progressive truncation of the chromosome. It is thought that telomeres may provide a buffer against this effect, at least until they are themselves eliminated by this effect.

Thus, the loss of telomeres may be part of programmed cell senescence and, conversely, the maintenance of telomeres may correspond to cell growth. These structures are maintained by an enzyme called telomerase. Telomerase contains RNA and protein components that act to synthesize telomeric sequences. If abnormal maintenance or proliferation of telomeres occurred, it is conceivable that unrestricted, i.e., neoplastic cell growth might result. Recently, there have been numerous reports lending credibility to this theory. For example, 94% of neuroblastomas tested in one study showed telomerase activity while normal adrenal tissue and benign ganglioneuromas did not (Hiyama et al., 1995). Similarly, Hiyama et al. (1995) found that over 80% of primary lung cancer tissues had telomerase activity while only 4.4% of normal tissues had activity. Chadeneau et al., (1995) found telomerase activity in colorectal cancer, but not in edematous polyps and Counter et al. (1994) reported telomerase activity in ovarian carcinoma. Abnormal telomerase activity also has been observed in tumors derived from skin, adipose, connective tissue, breast, stomach, pancreas, cervix, kidney, bladder, colon, prostate and blood (Kim et al., 1994).

Telomerase activity can be assayed by standard methods, which incorporate radioactive nucleotides into a substrate for telomerase followed by gel electrophoresis for analysis of the products formed. This conventional assay is difficult and insensitive, requiring about $10^7$ cells per assay (Morin, 1989). There are two known forms of telomerase—processive and non-processive. Processive telomerase adds multiple telomeric repeats to a DNA primer, while non-processive telomerase adds no more than one telomeric repeat to a DNA primer.

Kim et al. (1994) reported improved methods for the extraction and detection of telomerase activity. A detergent lysis method was modified to allow more uniform extraction of telomerase activity, even at low cell numbers. In addition, a PCR-based assay known as "TRAP" (telomeric repeat amplification protocol) was developed. This assay uses telomerase activity in a sample to generate telomerase-specific products which act as templates for amplification by polymerase.

Kim et al. (1994) allude to problems with respect to the PCR products generated. "Even under high stringency, staggered annealing of the downstream primer occurred (for example, annealing by three of the four repeats) . . . Thus, TRAP assay products do not directly reflect the distribution of telomerase products generated in the assay, and the interaction between the upstream and downstream primers must be prevented." As a result, TRAP can produce false-positive results and is not very quantitative. Additionally, the TRAP assay cannot distinguish or even properly detect non-processive telomerase activity. Therefore, there remains a need for a more reliable assay for telomerase activity in tissue samples.

SUMMARY OF THE INVENTION

Therefore, it is an object of the present invention to provide improved methods for the detection of processive and non-processive telomerase activities in tissue samples. It also is an object of the present invention to provide methods of quantitating these telomerase activities in tissues and determining the susceptibility of those cells to therapeutic intervention. It is a further object of the present invention to provide methods of screening for anti-telomerase activity, either for non-processive, processive or both, in candidate drugs.

In fulfilling these objects, there is provided a method for detecting and quantitating telomerase activity in a sample comprising the steps of: (i) obtaining the sample; (ii) contacting the sample with a telomerase primer and dNTPs; (iii) contacting a telomerase product of step (ii) with a first oligonucleotide and a second oligonucleotide under conditions permitting hybridization, wherein said first and said second oligonucleotides hybridize to said telomerase product such that no single-stranded region intervenes between said first and said second oligonucleotides; (iv) contacting the hybridized product and oligonucleotides with a ligase; and (v) detecting and quantitating the ligated form of said first and said second oligonucleotides.

In a preferred embodiment, steps (a) and (b) are repeated at least once prior to step (c). Specific embodiments are provided, wherein the ligated form is amplified by a ligase chain reaction. Further specific embodiments are provided for the electrophoretic separation of the ligated form.

Still further provided are methods wherein at least one of the first and second oligonucleotides contains a detectable label. Specific embodiments are provided wherein the label is selected from the group consisting of a radiolabel, a fluorescent label, a chemiluminescent label and a colorimetric label.

Yet another specific embodiment is provided wherein the first oligonucleotide further comprises a primer target attached to its 5' end and the second oligonucleotide comprises a PCR primer target attached to its 3'-end. In still another embodiment, a method is provided wherein the detecting further comprises contacting the ligated form with a polymerase, a 5' primer and a 3' primer, performing sequence specific amplification and identifying the amplification product. In a specific embodiment, the detecting method further comprises electrophoretic separation of the amplification product and in still further embodiments the amplification product contains a detectable label. Methods are provided wherein the label is selected from the group consisting of a radiolabel, a fluorescent label, a chemiluminescent label and a colorimetric label.

Also provided are methods wherein the sample is tumor tissue. In particular embodiments, there is provided a method wherein the tumor tissue is selected from the group consisting of, but not limited to, carcinomas of the breast, colon, esophagus, kidney, liver, lung, ovaries, prostate, stomach, uterus, pancreas and head and neck, sarcomas of bone and muscle, leukemias, myelomas, lymphomas, neuroblastomas, astrocytomas, gliomas, glioblastomas, retinoblastomas and melanomas. Specific embodiments provide the method further comprising the steps of: (vi) quantifying the telomerase activity of said sample; (vii) comparing the telomerase activity level with predetermined standards; and (viii) making a prognostic evaluation or clinical decision regarding the patient from which said tumor tissue was obtained.

Also provided are methods, wherein either the first or second oligonucleotide is attached to a support, at least the unattached oligonucleotide contains a detectable label and the detecting comprises identifying said label bound to the support. In particular embodiments, the attachment is effected by biotin/avidin. In still further embodiments, the label is a radiolabel, a fluorescent label, a chemiluminescent label and a colorimetric label.

A specific embodiment provides a method wherein the label is a fluorescent label and the linked oligonucleotide is labeled with a distinct fluorescent label such that the fluorescence of one label induces the fluorescence of the other label. In a further specific embodiment, the label is a β-emitting radiolabel and the support contains a scintillant. In another specific embodiment, the support is a bead.

There are also provided methods for incorporation of modified dNTPs including BrdUTP by telomerase. In a specific embodiment there is provided a method for determining telomerase by detection of BrdUTP covalently linked to the telomerase primer. In a further specific embodiment, the telomerase primer is attached to a support and the detecting comprises identifying BrdUTP linked to the support. In a particular embodiment, the identifying comprises contacting the support with an antibody that binds BrdUTP in a single-stranded polynucleotide, while not binding BrdUTP.

Methods are also provided wherein the antibody contains a detectable label selected from the group consisting of a radiolabel, a chemiluminescent label, a fluorescent label and a colorimetric label. Still further provided are methods wherein the antibody is linked to biotin followed by the binding of the biotin by avidin containing a detectable label.

A method for determining telomere length is also provided comprising the steps of: (i) providing a telomeric DNA; (ii) contacting the telomeric DNA with a plurality of oligonucleotides, under conditions permitting hybridization thereof, wherein the oligonucleotides hybridize to the telomeric DNA such that no single-stranded regions intervenes between the hybridized oligonucleotides; (iii) contacting the hybridized telomeric DNA and oligonucleotides with a ligase; and (iv) determining the length of the ligated form of the oligonucleotides.

Methods for obtaining an telomerase-inhbiting substance and detecting and quantitating telomerase-inhibiting activity of a substance are also provided comprising the steps of: (i) providing a telomerase preparation; (ii) contacting the telomerase preparation with a telomerase primer and dNTPs in the presence of one or more candidate inhibitor substances; (iii) quantitating telomerase product using ligation sequential reaction or BrdUTP incorporation; and (iv) comparing the amount of telomerase product of step (iii) with the amount of telomerase product synthesized in the absence of the substances.

In addition, the present invention provides for telomerase-inhibiting substances identified by a method having the steps of (i) providing a telomerase preparation; (ii) contacting said sample with a telomerase primer and dNTPs, wherein said dNTPs include BrdUTP or hapten-labeled nucleotides and said substance; (iii) determining the incorporation of BrdU or hapten-labeled nucleotides into a telomerase product of step (ii); and (iv) comparing the amount of telomerase product of step (ii) with the amount of telomerase product synthesized in the absence of said substance.

In yet another embodiment, there is provided a method for detecting and quantitating specific forms of telomerase, either processive or non-processive, including the steps of (i) providing a telomerase preparation; (ii) contacting the telomerase preparation with a double repeat 12mer oligonucleotide plus dNTPs in one reaction, and as single repeat 6mer oligonucleotide plus dNTPs in another reaction; (iii) detecting the telomerase products. In one embodiment, the relative amounts of processive and non-processive activity can be compared by comparing the amounts of 12mer- and 6mer-primed products.

Another method for specifically detecting processive telomerase activity comprises the steps of (i) providing a telomerase preparation; (ii) contacting the telomerase preparation with a telomeric repeat oligonucleotide with a 3'-end having the repeat GGTTAG or a sequence complementary to residues at the 5'-end of a telomerase template sequence. In one embodiment, the relative amounts of processive and non-processive activity can be compared by comparing the amounts of telomerase product primed with a standard primer and the primer having either the 3'-end repeat GGTTAG or a sequence complementary to residues at the 5'-end of a telomerase template sequence.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
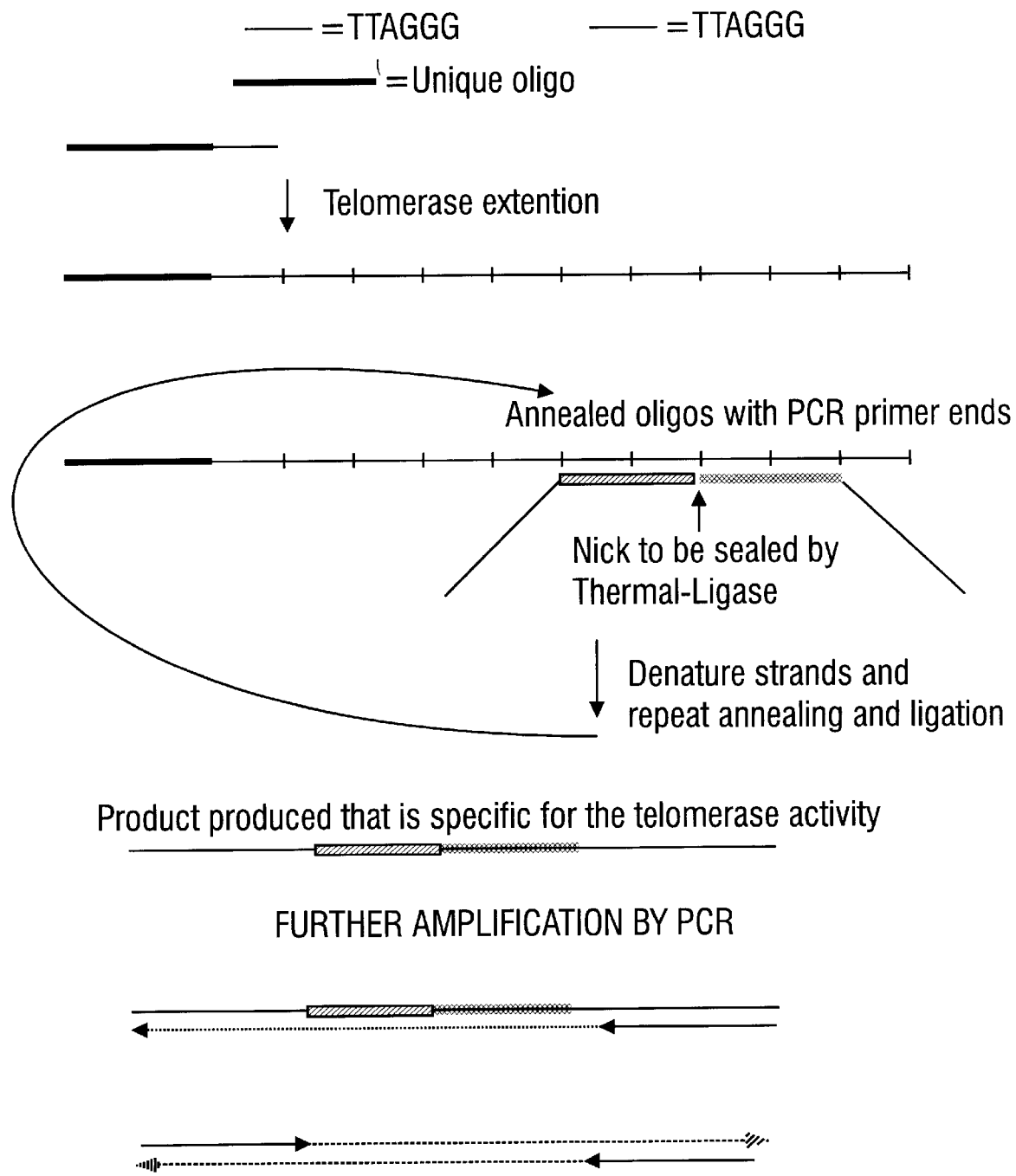
FIG. 1: Principle of Ligation Based Assay for Telomerase. A diagram outlining the general approach of LSR.

The present invention provides improved methods for characterizing processive and non-processive telomerase activities in a variety of samples. The assay can be applied to the diagnosis of cancer, for example, where a tissue sample may contain neoplastic or malignant cells, it now is possible to easily, accurately and sensitively screen for the specific form of telomerase activity in such a sample. There also is a further application of the present invention in the prognostic evaluation of patients. Depending on the extent and kind of telomeric activity in a given sample, it is possible to predict the clinical course of the patient from which the sample was derived. Finally, the assay can be used to screen compounds for anti-telomerase activity and, therefore, for potential as anti-cancer agents.

I. Outline of a Telomerase-Specific Assay

Telomerase is made up of a ribonucleoprotein complex that utilizes a region of the enzyme's RNA component as a template for synthesis of a repeating nucleotide unit that is added to the end of chromosomes. In humans, the six-mer TTAGGG is the repeating unit, as it is in mice. In contrast, Tetrahymena telomerase produces six-base repeats that consist of the sequence TTGGGG. Though possible sequence requirements for telomerase substrate have not been completely elucidated, human telomerase acts on a single stranded primer comprised of at least one or two units of TTAGGG, although almost any sequence may suffice to a lesser extent.

In one aspect, the present invention relies on a unique, ligation-dependent amplification reaction to identify telomerase products. A sample is obtained and treated to isolate a telomerase-containing fraction. This fraction is contacted with a telomerase primer, and the reagents necessary for telomere synthesis, under conditions supporting telomerase activity. After a sufficient period of time, depending on the subsequent methods employed, detection of telomerase products is performed. This is accomplished by hybridizing two oligonucleotides which anneal immediately adjacent to one another on the telomerase product. The sequences of these primers preferably differ such that their ends fall at different positions within the repeat sequence. Whether the same or different, at least one will have a 5'-phosphate residue. Following treatment of the mixture with DNA ligase, the ligated oligonucleotides may be detected by a variety of mechanisms. It is important to note that the design of the telomerase primer and the oligonucleotides is such that a ligation product will be generated only if the telomerase has acted upon the primer. The details of this method are outlined below.

II. Isolation of Telomerase-Containing Fractions from Samples

A variety of different cell types may be screened for telomerase activity. In terms of cancer diagnostic applications, samples may be derived from tissues or fluids. For example, the body tissue can be bone marrow aspirate, bone marrow biopsy, lymph node aspirate, lymph node biopsy, spleen tissue, fine needle aspirate, skin biopsy or organ tissue biopsy. Fluid samples include peripheral blood, lymph fluid, ascites, serous fluid, pleural effusion, sputum, cerebrospinal fluid, lacrimal fluid, stool or urine.

Telomerase preparations are generated by disrupting cells, preferably releasing intact nuclei that leak telomerase into the extract. Several different methods have been applied and all work acceptably well. Multiple freeze-thaw is the easiest, while use of detergent-based (e.g., NP40) protocols is less than ideal as detergents tend to be carried throughout subsequent reactions. However any method that yields an extract like the S-100 extract typically used for telomerase assays would be sufficient.

III. Ligase sequential Reaction

One of the problematic aspects of measuring telomerase activity has been the identification of a telomerase product. Previously, this has been accomplished by either incorporation of radioactively labeled nucleotides into the telomere product or by direct PCR of telomerase product, as reported by Kim et al. (1994). As discussed above, however, these approaches have proved problematic. For example, the PCR assay cannot detect non-processive telomerase activity and cannot distinguish between the two forms of telomerase, while the conventional assay is insensitive, difficult and costly. Using direct PCR of the product results in PCR products that are not representative of the telomerase products. For the PCR assay, the ability to quantitate the results is limited.

The present invention avoids the problems associated with the direct PCR approach by using a ligase-dependent reaction designated as ligase sequential reaction, or LSR.

LSR relies on the design of both the telomerase primer and a pair of oligonucleotides specific for a telomerase product. The linear amplification of LSR ensures good quantitation as opposed to exponential amplification as the initial method of amplification. In one embodiment, the telomerase primer is a doublet of the six-mer TTAGGG, hence:

5'-T-T-A-G-G-G-T-T-A-G-G-G-3' (SEQ ID. NO:1)

Alternatively, a single TTAGGG repeat may be used, at least for the class of telomerase now called processive telomerase. The present inventors have found that these telomerases add many telomeric repeats, as many as thirty or more, in cell free extracts. This form of telomerase is very efficient and aggressive in synthesizing telomeric DNA. Non-processive telomerases, on the other hand, add only one telomeric repeat or a partial repeat to primed DNA. This form of telomerase is not very efficient or aggressive. The increase in processivity appears to occur frequently in cancer cells as a mechanism to quickly regenerate and maintain their telomeres.

If the telomerase activity is non-processive the 12 base oligonucleotide primer and the 6 base primer will be extended by 6 or less bases only (for all permutations of the TTAGGG repeat sequence). The extended 12-mer is sufficiently long to be detectable by LSR while the extended six-mer is not. For the 12-mer, as little as six added bases can be detected. For the 6-mer, as little as 12 added bases can be detected. If the telomerase is processive, both primers will be elongated sufficiently for detection by LSR. This technique allows for not only the detection of non-processive telomerase activity but the differentiation of such activity from a processive mechanism.

The oligonucleotides are at least the complement of this sequence, or:

3'-A-A-T-C-C-C-A-A-T-C-C-C-5' (SEQ ID. NO:2)

The oligonucleotides also may contain additional copies of the AATCCC repeat.

Where a telomerase has acted upon the primer (1), a typical extension product will appear as:

5'-T-T-A-G-G-G-T-T-A-G-G-G-T-T-A-G-G-G-T-T-A-G-G-G . . . -3' (SEQ ID. NO:3)

The bold portion indicates that region of the product (SEQ ID. NO:3) synthesized de novo by the telomerase. Subsequent hybridization of the exemplified oligonucleotides (SEQ ID. NO:2) results in the following hybridization product:

5'-T-T-A-G-G-G-T-T-A-G-G-G-T-T-A-G-G-G-T-T-A-G-G-G . . . -3' (SEQ ID. NO:3)
3'-C-C-C-A-A-T-C-C-C-A-A-T-C-C-C A-A-T-C-C-C-A-A-T-C-C-C-5' (SEQ ID. NO:4; SEQ ID. NO:5)

(Note the absence of a bond between the two oligonucleotides.) Treatment of the hybridization product with ligase will result in the covalent bonding of the 3'-end of the first oligonucleotide and the 5'-end of the second oligonucleotide (the only other requirement for this reaction is necessary that the 5'-end of the second oligonucleotide carry a phosphate residue):

5'-T-T-A-G-G-G-T-T-A-G-G-G-T-T-A-G-G-G-T-T-A-G-G-G . . . -3' (SEQ ID. NO:3)
3'-C-C-C-A-A-T-C-C-C-A-A-T-C-C-C-A-A-T-C-C-C-A-A-T-C-C-C-5' (SEQ ID. NO:6)

Subsequent release of the strands of the ligase-treated hybridization product will result in a new product:

3'-C-C-C-A-A-T-C-C-C-A-A-T-C-C-C-A-A-T-C-C-C-A-A-T-C-C-C-5' (SEQ ID. NO:6)

This reaction can be repeated through multiple rounds of temperature cycling so long as sufficient free oligonucleotides are available and the ligase is thermostable. Additional ligase may be added during the course of the reaction to increase the cycling time.

In a modification of this embodiment, a primer is provided that contains a TTAGGG repeat at the 3'-end and a unique sequence at the 5'-end:

5'-[unique sequence]-TTAGGG-3'

Extension of this primer with telomerase will result in a telomerase product:

5'-[unique sequence]-T-T-A-G-G-G-T-T-A-G-G-G-T-T-A-G-G-G-3' (SEQ ID. NO:7)

Rather than detect using the complement of repeats, the detection takes advantage of the unique sequence, using oligonucleotides complementary to the telomeric repeats and the unique sequence:

5'-[unique sequence]-T-T-A-G-G-G-T-T-A-G-G-G-T-T-A-G-G-G-3' (SEQ ID. NO:8)
3'-[unique complmnt] A-A-T-C-C-C-A-A-T-C-C-C-A-A-T-C-C-C-5' (SEQ ID. NO:9)

(Note the absence of a bond between the two oligonucleotides). Treatment of the hybridization product with ligase will result in the covalent bonding of the 3'-end of the telomeric complement oligonucleotide and the 5'-end of the unique complement oligonucleotide (the only other requirement for this reaction is necessary that the 5'-end of the unique complement oligonucleotide carry a phosphate residue):

5'-[unique sequence]-T-T-A-G-G-G-T-T-A-G-G-G-T-T-A-G-G-G-3' (SEQ ID. NO:8)
3'-[unique complmnt]-A-A-T-C-C-C-A-A-T-C-C-C-A-A-T-C-C-C-5' (SEQ ID. NO:9)

Subsequent release of the strands of the ligase-treated hybridization product will result in a new product:

3'-[unique complmnt]-A-A-T-C-C-C-A-A-T-C-C-C-A-A-T-C-C-C-5' (SEQ ID. NO:9)

This reaction can be repeated through multiple rounds of temperature cycling so long as sufficient free oligonucleotides are available and the ligase is thermostable. Additional ligase may be added during the course of the reaction to increase the cycling time. The advantage of this approach is that, because the detection relies on the presence of the unique sequence, only products resulting from extension of the primer are detected, and not products resulting from other contaminating telomeric primers.

IV. Template Dependent Amplification Processes

In a variation on the foregoing process, it is possible to use other template dependent amplification processes to further amplify the initial ligation product. One of the best known of these amplification methods is the polymerase chain reaction (PCR), which is described in detail in U.S. Pat. Nos. 4,683,195, 4,683,202 and 4,800,159, and in Innis et al., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated.

In the present invention, PCR could be applied as follows. The oligonucleotides will be modified to carry PCR target regions. Two different kinds of additions would be needed. First, a first PCR target would be joined at the 5'-end of the first oligonucleotide and another at the 3'-end of the second oligonucleotide; the purpose of this arrangement is to produce a hybridization product with PCR targets at its end, but not at the junction between the hybridized oligonucleotides. After ligation has occurred, the correctly oriented ligation product is released from the telomerase product by heating. Next, a first PCR primer, specific for the target sequence attached to the second oligonucleotide, is contacted with the ligation product, a polymerase and the necessary dNTPs. The primer is extended, released from the ligation product by heating and contacted with a second PCR primer specific for the target sequence attached to the first oligonucleotide. This primer is, in turn, extended, released and subsequent rounds of thermocycling result in amplification of the original ligation product. A diagram of this process is illustrated in FIG. 1.

Figure 2:
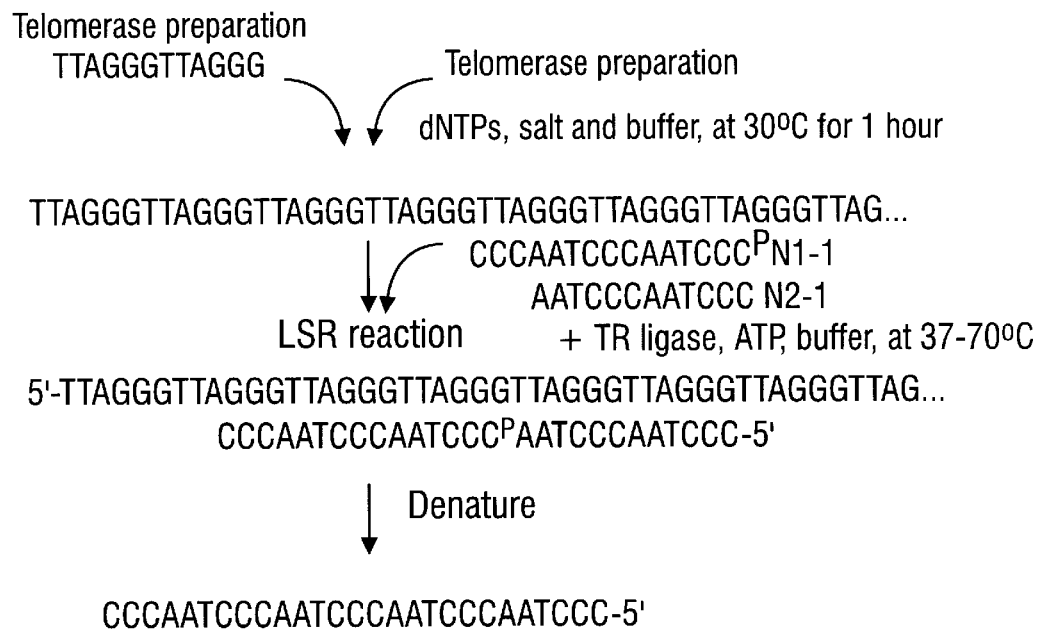
FIG. 2: Diagrammatic Representation of Telomerase-Specific Assay. A flow chart illustrates starting primers and reaction products using both a ligation sequential reaction (LSR) and a polymerase chain reaction (PCR).

This process is outlined in more detail in FIG. 2 where an oligonucleotide (telomerase primer) with a telomeric-like sequence is presented to the telomerase preparation. The primer is extended by the telomerase using the telomerase RNA as a template. The sequence synthesized is specific for the particular telomerase. The telomerase primer can be almost any sequence although the sequence 5'-TTAGGGTTAGGG-3' (SEQ ID. NO:1) or 5'-TTAGGG-3' is preferred. The telomerase reaction is stopped by heat or other means of inactivation and the extended DNA can be detected by LSR. Two oligonucleotides, shown as N1-1 and N2-1 in FIG. 2, are annealed to the telomerase product such that there is only a nick space between them. The N1-1 oligo is 5'-phosphorylated to allow for subsequent ligation. The phosphorylated oligo should preferably contain a few extra bases that the unphosphorylated oligo does not have. This will prevent the phosphorylated oligo from ligating to itself and creating ladders that may not represent the telomerase product. The specificity of annealing can be optimized by variation of the salt conditions and temperature. The use of thermal-resistant ligase allows for more stringent annealing at higher temperatures. The sequences of N1-1 and N2-1 will vary depending on the telomerase target sequence. More product can be produced by denaturing and repeating the annealing and ligation process as many times as necessary.

This process can also be modified where the two annealing oligonucleotides have additional sequences on their ends to allow for PCR (Polymerase Chain Reaction) amplification. In FIG. 2 these oligos are referred to as N1'-1 and N2'-1. As with N1-1 and N2-1 the two oligos are annealed and ligated in the LSR reaction. The unique sequences placed on the ends additionally serve to avoid unwanted primer self annealing as described above. The product can now be amplified further by PCR using the PCR primers N1'-2 and N2'-2. These primers need only be distinct from cellular sequences and can be optimized for efficiency with low background.

Another method of sequence-specific amplification is the ligase chain reaction (LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence. This approach could be applied to the present invention any time after the first round of LSR.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker et al., 1992) incorporated herein by reference in its entirety, may also be useful in the amplification of nucleic acids in the present invention.

Strand displacement amplification (SDA) is another method of carrying out isothermal amplification of nucleic acids which involves multiple rounds of strand displacement and synthesis, i.e., nick translation. A similar method, called repair chain reaction (RCR) involves annealing several probes throughout a region targeted for amplification, followed by a repair reaction in which only two of the four bases are present. The other two bases can be added as biotinylated derivatives for easy detection. A similar approach is used in SDA.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Davey et al., European Patent Application Publication No. 329,822, incorporated herein by reference in its entirely, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, and RNase specific for RNA in duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of E. coli DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can the re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700, incorporated herein by reference in its entirely, disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" disclosed by Frohman, (1990), and "one-sided PCR" (Ohara et al., (1989), all references herein incorporated by reference in their entirety.

V. Methods of Detecting Ligation and Amplification Products

Following generation of the ligation product and amplification by a selected means, it is necessary to detect the reaction products in order to determine if telomerase activity is present in a sample or, in the case of assessing telomere length, to measure the size of the resulting product. A variety of different methods for detection are available, but some rely on physical separation of the reaction products from the template (telomerase primer or telomere).

Figure 3:
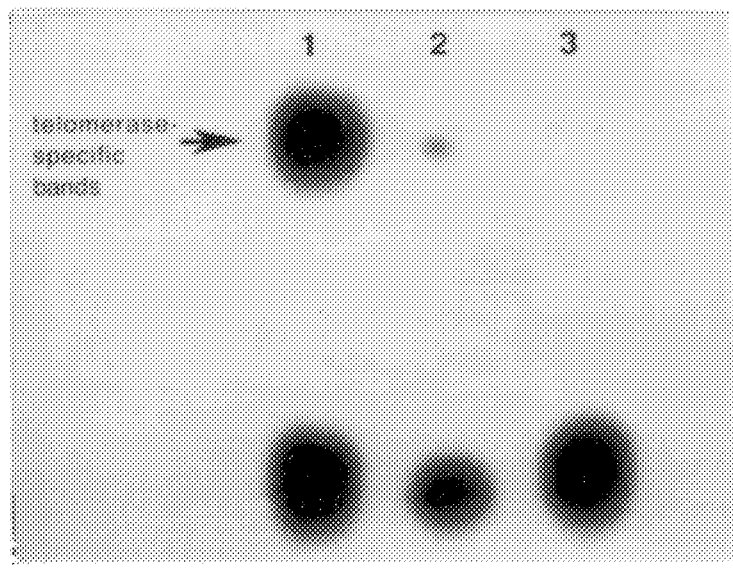
FIG. 3: Telomerase-Specific Assay. The LSR-PCR assay was performed on a cell sample known to contain telomerase by the conventional telomerase assay. Lane 1 is the experimental reaction and contains two major bands: the lower band is a telomerase-independent band that was used as a control for the reaction and the upper band is the 60 bp fragment that is specific to the telomerase product. Lane 2 is a control, RNAse treated telomerase sample. Lane 3 is a control, unreacted telomerase preparation.
Figure 4:
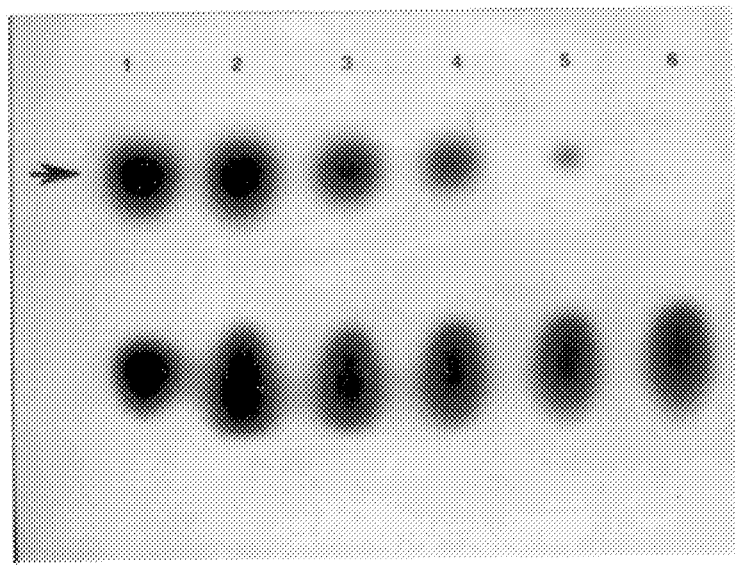
FIG. 4: Quantitation of Telomerase by the LSR-PCR Assay. The LSR-PCR assay was performed on telomerase preparation that contained 100 cells (lane 1), 50 cell (lane 2), 25 cells (lane 3), 12 cells (lane 4), 6 cells (lane 5) and no cells (lane 6).

The standard separation technique is gel electrophoresis, where products are separated by differential migration through a gel matrix such as agarose or acrylamide. For the detection of low molecular weight species, gel concentrations of about 1.0–4.0% for agarose and 8–15% for acrylamide are preferred. The ligation products will consist of multiples of the oligonucleotide and, depending on the intensity, will vary according to the amount of telomerase activity as shown in FIG. 4. The LSR product will appear as a 27-base pair fragment following electrophoresis. Following LSR-PCR, a 60-base pair product is observed as shown in FIG. 3. The absence of telomerase activity will be indicated by the absence of any ligation or amplification product, i.e., the presence of only unligated oligonucleotide.

An alternative approach that would be amenable to screening and automation would be non-electrophoretic separation of ligation products. The LSR product in some cases need not be separated from starting material. For example, the SPA™ (scintillant proximity assay) technology (Amersham) avoids the need for separation steps. In this system one oligo contains a β-emitter and the other oligo is attached to a scintillant bead or matrix. Light is emitted only when the two oligos are joined. The same general approach is possible using fluorochrome quenching and secondary fluorescence.

Figure 6:
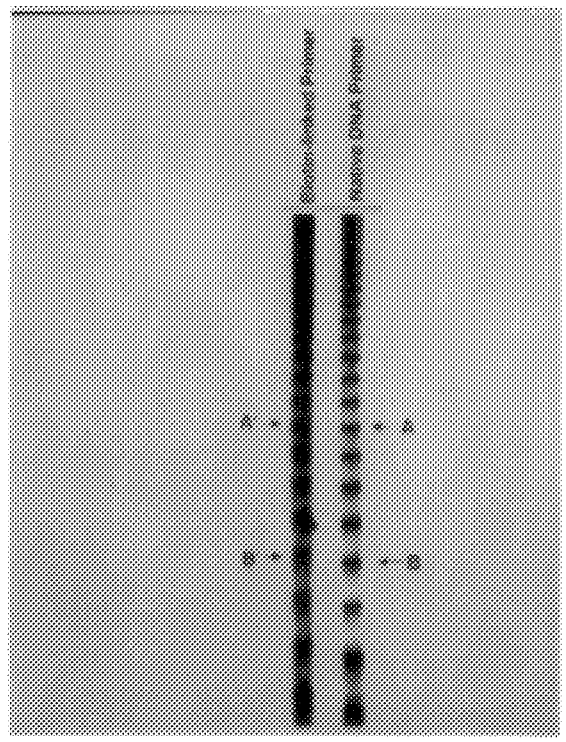
FIG. 6: Telomerase Extension of a Biotinylated 5'-End Labeled Primer. A biotinylated primer is compared to an unmodified primer when used as a substrate for telomerase. A and B are selected extension products using the native primer and A' and B' are the corresponding extension products generated using the biotinylated primer.
Figure 7:
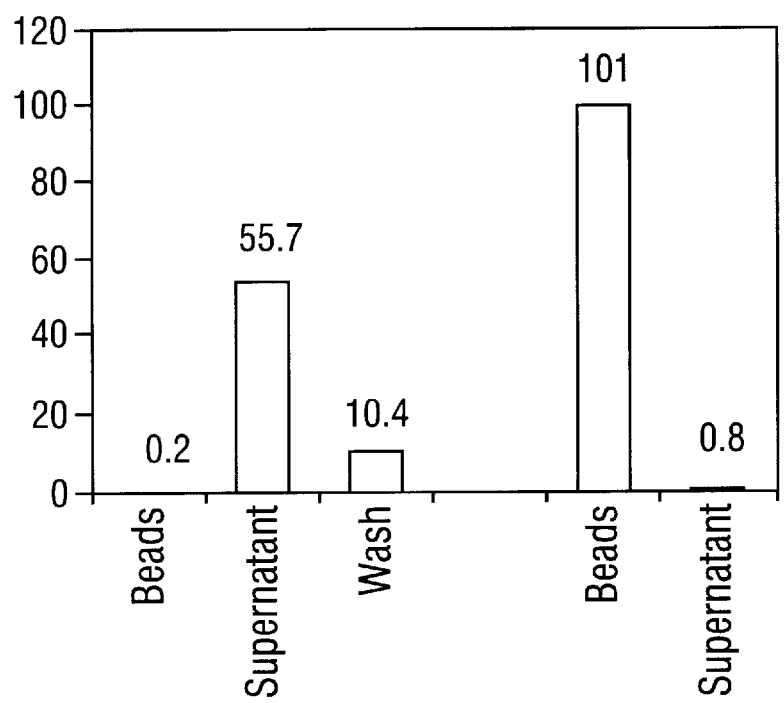
FIG. 7: Purification of Biotin-labeled Primer by Magnetic Streptavidin Beads. A rapid and simple assay for telomerase activity.

In certain applications, separation may be required. In these instances, a method for separation could be used where a biotinylated oligo permits subsequent binding to immobilized avidin. As shown in FIG. 6, a 5'-biotinylated primer is used efficiently as a telomerase substrate. Separation of the product can be conducted using magnetic avidin or streptavidin beads, as shown in FIG. 7.

Of course, separation of the products is only part of the detection process, as one must be able to determine the nature of the products. In the gel electrophoresis method, this is done by actual visualization of the bands in the gel. This can be accomplished by staining the gel with ethidium bromide or other DNA binding, auto-fluorescing compound. Excitation with the appropriate wavelength (e.g., ultraviolet) causes the bound auto-fluorescing compound to emit visible light, identifying the location of DNA within the gel. An alternative is labeling of the ligation products with a chromophore, fluorophore or radiolabel. These labels may be detected by chemical reaction, light excitation or emission, respectively. Again, the signal indicates the location of the DNA within the gel. With the use of appropriate standards, one can estimate the size of the identified DNA's.

If a column (spin or chromatographic) approach is used, the existence of a product in the phase where only higher molecular weight species should exist is positive result for telomerase activity. Again, the DNA can be identified by the use of an auto-fluorescing chelating agent. Alternatively, a chromophore, fluorophore or radiolabel attached to the product can serve to identify the presence of product.

VI. Alternative Methods for Detection of Telomerase Activity

Figure 8:
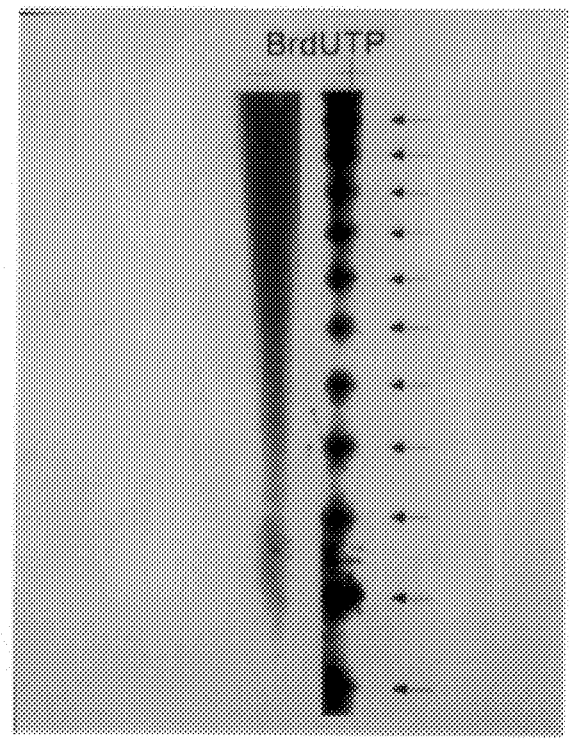
FIG. 8: Telomerase Activity in the Presence of BrdUTP. Demonstration of the use of BrdUTP as a substrate for telomerase is provided. (+) indicates the presence of BrdUTP and (−) indicates the absence thereof.

The inventors have determined, again surprisingly, that telomerases can incorporate modified nucleotides, such as bromodeoxyuridine triphosphate (BrdUTP), into the telomerase product as shown in FIG. 8. This offers a significant advantage over the complications involved with handling radioactive labels. Additionally, more sensitive assays can be run using antibody amplification of the signal. As few as 250 molecules of BrdUTP have been detected with fluorescently labeled antibodies against BrdUTP. Each telomerase enzyme can incorporate about a hundred or more BrdUTP nucleotides into the product, which allows for the detection of as few as 3 molecules of the telomerase enzyme. This means that if a single cell contains 3 or more molecules of telomerase, it should be detectable by this method. Besides fluorescent labels, the antibody may contain labels such as colorimetric, chemiluminescent or radioactive ones.

BrdU detection with labeled antibodies allows another advantage, namely, providing for specific detection of telomerase over other polymerases that may be present. This is due to the fact that BrdUTP is incorporated into single-stranded DNA by telomerase while endogenous polymerases will incorporate BrdUTP into double-stranded DNA. The antibodies directed against BrdU will only recognize the BrdU when it is in single-stranded DNA and not duplex DNA. This allows for the performance of the assay without purification of the telomerase.

Figure 5:
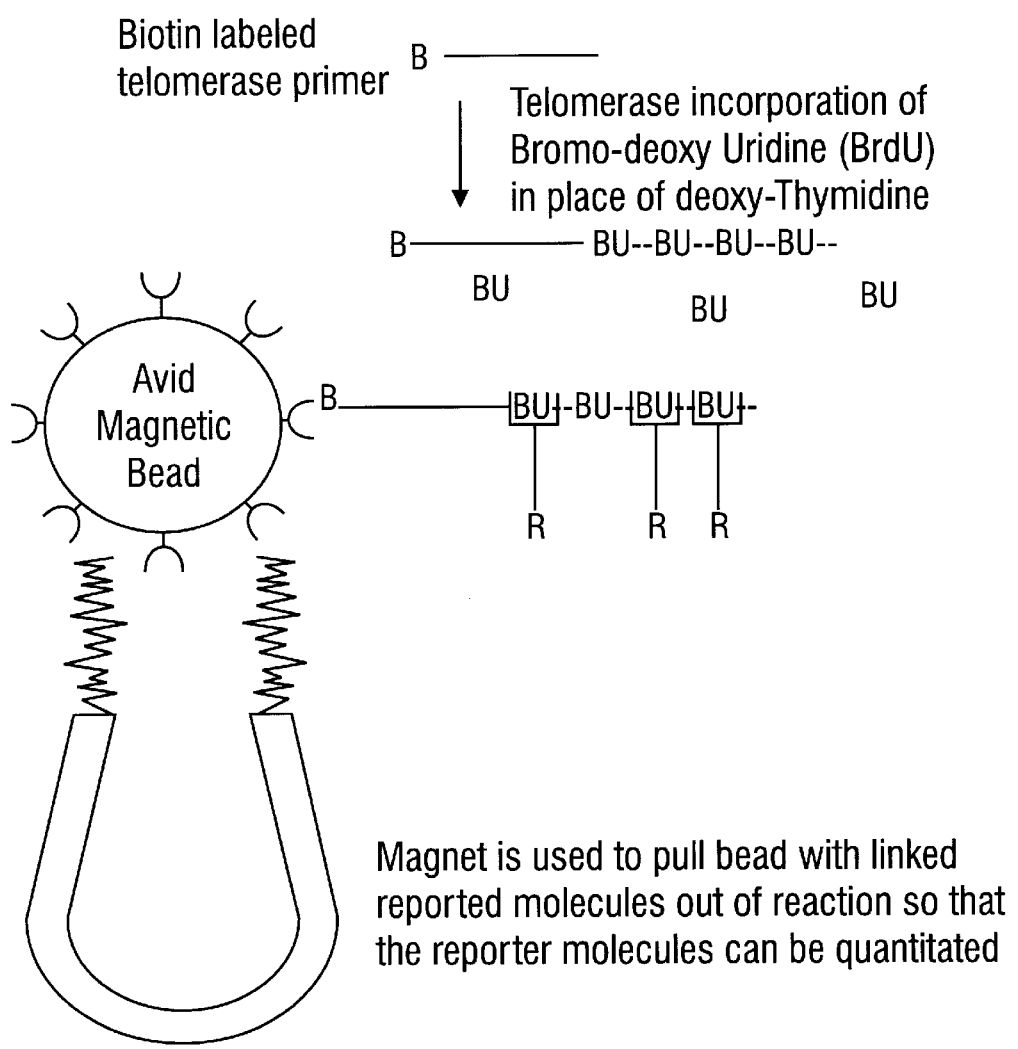
FIG. 5: A Rapid Assay for Telomerase using BrdUTP Incorporation Combined with a Biotin-Avidin Separation System. A diagram illustrating the use of both the BrdUTP incorporation and biotin-avidin separation.

For use as a quantitative assay, the amount of BrdU incorporated into the telomerase product can be measured by gel electrophoresis. A combination of BrdU detection, biotin-labeled primers and magnetic streptavidin bead separation is diagrammed in FIG. 5. This represents a rapid, sensitive and simple assay for telomerase.

It also has surprisingly been found that a processive telomerase adds sequences a primer ending with the first G residue of the TTAGGG repeat, e.g., TTAGGGTTAG (SEQ ID. NO:1), whereas a non-processive telomerase will not add sequences to this primer. This observation makes it possible, for the first time, to detect and quantitate only processive telomerase, even in the presence of non-processive telomerase. While the LSR method is preferred, any telomerase assay may be applied to determine specific processive telomerase activity using this specific primer.

The reason for this striking and selective effect appears to be due to the fact that the RNA template sequence of human telomerase ends at the 5' end with the complement of the sequence GGTTAG. The non-processive telomerase can bind the oligo ending 3' with GGTTAG so that there is maximum base-pairing and maximum stability, as shown below:

DNA PRIMER    5'-GTTAGGGTTAG-3'    (SEQ ID. NO: 11)

RNA TEMPLATE    3'-CAAUCCCAAUC-5'    (SEQ ID. NO: 12)

Because the primer reaches to the end of the template, the telomerase can not add anymore sequence to the primer unless the primer is unwound from the template, repositioned and base-paired further down toward the 3' end of the template, as show below:

DNA PRIMER    5'-GTTAGGGTTAG    (SEQ ID. NO: 11)

RNA TEMPLATE  3'-CAAUCCCAAU-5'  (SEQ ID. NO: 12)

The open template sequence is then read by the telomerase and new sequence is added to the primer until the end of the template sequence is reached, as shown below where new added sequences are in bold:

DNA PRIMER    5'-GTTAGGGTTAGGGTTAG-3' (SEQ ID. NO: 13)

RNA TEMPLATE  3'-CAAUCCCAAUC-5'    (SEQ ID. NO: 12)

Non-processive telomerase does not perform this process of unwinding and repositioning, consistent with its being non-processive, yet processive telomerase will repeat this process multiple times, consistent with its being processive. Thus, processive telomerase can add labeled or detectable sequence to the GGTTAG primer, while non-processive telomerase adds nothing. Therefore, the activity generated by this reaction detects only the more aggressive, processive form of telomerase.

VII. Modification of LSR for the Measurement of Telomere Length

The telomerase activity assay described above may advantageously be modified to determine the length of telomeres in a given cell sample. At least one model proposes a direct relationship between length of telomeres and the mortality of cells. Rhyu (1995) proposes that as cell divisions occurs, telomeres gradually are eliminated. When normal cells reach a critical number of telomeres, senescence occurs. For other cells in which the ability to detect abnormalities has been lost, further loss of telomeres, along with chromosome breaks and translocations occurs. In some of these cells, telomerase is reactivated and the mutated chromosomes are stabilized, i.e., become immortal.

Standardized methodology for isolation of nucleic acids may be applied to the instant invention for the purpose of isolating telomeric sequences, e.g., Maniatis (1982). For example, cells may be disrupted by physically by boiling or freeze-thawing or by chemical means, such as ionic detergents. Treatment of cells with proteinase K may be applied to remove contaminating proteins. Phenol/chloroform extraction also provides a method for further purification of the nucleic acids.

Once telomeric DNA is isolated, the DNA is contacted with 5'-phosphorylated oligonucleotides comprising at least two copies of the telomeric repeat under conditions permitting hybridization thereof. Then, the hybridization product is contacted with a ligase and then denatured from the telomeric DNA by heating. Subsequently, the ligation product is further amplified by repeating the hybridization, ligation and heating steps. Ligation products are then detected.

VIII. Obtaining Anti-Telomerase Substances

Another way in which the present invention may be employed is in the obtaining of drugs having anti-telomerase activity. Because telomerase reactivation appears to be a widespread occurrence in malignant cells, the ability to inhibit telomerase activity in these cells may well provide a novel chemotherapeutic approach. In addition, the absence of telomerase activity in most normal cell types means that such an intervention would be highly specific for cancer cells.

Like the assay described above, the first step would be the isolation of telomerase. Here, however, a tissue source known to produce significant quantities of active telomerase would be used. Suitable cells lines producing telomerase included HeLa, 293 or WI38VA13 cells, but could be almost any immortalized cell. Any of the procedures described above for isolation may be applied.

The telomerase preparation then is contacted with a telomerase primer but, in this instance, the reaction mixture also will include a putative telomerase inhibitor. Preferably a range of concentrations will be used. This range will be determined by the class of compound being tested but generally will be between 1 nM and 1 mM. Detection of telomerase product may be by any of the means described above.

Appropriate controls will need to be performed in order to ensure accuracy of the results. Obviously, a positive control will consist of telomerase preparation including no drug. AZT triphosphate is a known inhibitor or telomerase and can be used as a positive control.

In some situations, it may be desirable to identify and obtain substances that are specific for one form of telomerase (processive versus non-processive) over the other. For example, some non-processive activity may be desirable in normal cells and, therefore, selective abrogation of processive activity may provide therapeutic advantages, such as minimized toxicity to normal cells.

IX. Clinical Correlations

Telomere length in cancer cells, where many cells are immortal, apparently depends on both the loss of telomeric repeats as a result of chromosome replication and the reactivation of telomerase. In most cancers, telomeres have shortened considerably prior to rise of telomerase activity. Presumably, in those cells where telomerase cannot keep pace with chromosomal shortening, the cells will die. On the other hand, extension of shortened telomeres may result in the continued proliferation of cells.

In at least one case, there was an effort to correlate telomerase activity with the clinical stage of cancer and the patient's prognosis. Hiyama et al. (1995) found that in advanced neuroblastomas correlated with high telomerase activity. In a comparison of stage IVS neuroblastomas, 7 out of 8 patients had low or undetectable telomerase activity and these patients' tumors all regressed. The eighth patient, who had high telomerase activity, died.

X. Kits

The reagents of the present invention may be provided in the form of kits for use in any of the foregoing assays. The kits would include reagents for assaying either processive or non-processive telomerase. For example, included in the kit for LSR and PCR might be cell lysis buffer, oligonucleotides, ligase, ligase reaction buffer, polymerase and polymerase buffer, RNase and a telomerase control sample. Container means may be provided to hold any of the foregoing compositions, and include at least one vial, test tube, flask, bottle or syringe. The kits also may include a blow-molded plastic container in which the desired vials are retained.

XI. Examples

EXAMPLE 1

Preparation Of Telomerase Sample

Cells are treated with lysis buffer (10 mM Tris, pH 7.5, 1 mM $MgCl_2$, 1 mM EGTA, 0.1 mM PMSF, 5 mM BME, 10% glycerol in DEPC-treated water plus RNA-guard™ (5 U/ml) ). The cells are placed in liquid nitrogen until frozen, then placed in a 37° C. water bath until thawed. This process is repeated up to five times.

EXAMPLE 2

Telomerase Reaction

A 40 μl telomerase assay was conducted using 20 μl of the telomerase preparation. The reaction components were added to the mixture:

| | |
|---|---|
| Tris-Cl (8.5) | 50 mM |
| K-OAc | 50 mM |
| MgCl$_2$ | 1.0 mM |
| BME | 5.0 mM |
| spermidine | 1.0 mM |
| dATP | 50 μM to 2 mM |
| dTTP | 50 μM to 2 mM |
| dGTP | 1 μM to 2 mM |
| Telomerase primer | 1 μM |

The reaction was allowed to proceed for 1 hour at 30° C.

If labeled nucleotides are incorporated the reaction can be assayed. If further manipulations are required the mixture is treated with RNase to stop the reaction and proteinase K, phenol and precipitated by ethanol.

The general variables are that the telomerase reaction can be done at higher or lower temperatures 25°–45° C., and the nucleotides can be high or low, 1 μM to 2 mM. The variability in the nucleotide concentration is very restricted by the standard assay but the inventor's assay allows testing of virtually any concentration. The other ingredients in the assay are mostly dispensable except for Mg. The time of reaction can run for hours and more product can be made.

EXAMPLE 3

Annealing And Ligation Of Primers (LSR)

A 20 μl reaction was carried out where 5' phosphorylated Primer A-5'-CCCTAACCCTAATGTACAAGACTAG TGTCA-3' (SEQ ID. NO:14) and
Primer B-5'-CGGCGTACACGGAGCTGACCCTAACCC TAA-3' (SEQ ID. NO:15) were added to the telomerase product in a ligation buffer containing:

| | |
|---|---|
| 20 mM | Tris-HCl (pH 8.5 at 25° C.) |
| 25 mM | KCl |
| 10 mM | MgCl$_2$ |
| 0.5 mM | NAD |
| 0.01% | TRITON-X-100 ™ detergent |
| 100 ng | Primer A |
| 100 ng | Primer B |
| 5 units | Thermostable DNA ligase |

The reaction is then subjected to 40 cycles of the following regimen: 45 seconds at 94° C., 10 seconds at 36° C.

The ligation can take place at virtually any temperature from 25° C. to 80° C. The 36° C. temp is determined by the 12 bases of annealling that is necessary. The longer the sequence the higher the temperature.

EXAMPLE 4

PCR Amplification

Amplification of the LSR product was then carried out according to the following protocol:

To 1–100 μl of the LSR product was added 50 to 100 μl of:

| | |
|---|---|
| 50 mM | KCl |
| 10 mM | Tris-HCl (pH 9.0 at 25° C.) |
| 1% | TRITON-X-100 ™ detergent |
| 2.0 mM | MgCl$_2$ |
| 1 mM | dNTPs |
| 100 ng | Primer A* |
| 100 ng | Primer B* |

2.5 Units of Taq Polymerase was added to initiate the reaction and the mixture was subject to 30 cycles of amplification of the following regimen: 94° C. 1 minute, 65° C. 1 minute and 72° C. 1 minute.

| | |
|---|---|
| Primer A* = 5'-TGACACTAGTCTTGTACA-3' | (SEQ ID. NO:16) |
| Primer B* = 5'-CGGCGTACACGGAGCTGA-3' | (SEQ ID. NO:17) |

The PCR conditions can be changed considerably in the nucleotides, primers, and Mg concentrations. The temperature can range form 25° C. to 80° C. for polymerizing.

EXAMPLE 5

Results

The LSR-PCR assay was performed on a cell sample known to contain telomerase by the conventional telomerase assay. Lane 1 contains two bands. The lower band is a telomerase-independent band that was used as a control for the reaction and the upper band is the 60 bp fragment that is specific to the telomerase product. The signal produced comes from 100 cells. The telomerase contains a critical RNA component that, when digested with RNAse, destroys telomerase activity. As a control, the inventors predigested the telomerase preparation with RNase and performed the telomerase reaction followed by the LSR-PCR assay. Lane 2 contains this sample and can be seen not to contain the telomerase-specific 60 bp band. Lane 3 is a telomerase preparation that was not allowed to go through the telomerase reaction yet was assayed by the LSR-PCR assay. Again there is no telomerase-specific band.

The LSR-PCR assay was performed on telomerase preparation that contained 100 cells (lane 1), 50 cell (lane 2), 25 cells (lane 3), 12 cells (lane 4), 6 cells (lane 5) and no cells (lane 6). The intensity of the telomerase-specific 60 bp band is directly dependent on the amount of telomerase present or the number of telomerase-producing cells. Lane 5 illustrates that as few as 10 cancer cells can be detected using conservative measures for amplification. Using additional rounds of amplification allows for the detection of a single cancer cell.

As shown in FIG. 6, a 5'-biotinylated primer was used in the telomerase reaction and compared to unlabeled primer. Both products were labeled with $^{32}$P for detection. The autoradiogram shows that the biotin linked primer is used efficiently as a telomerase substrate. Following the use of a biotinylated primer, a separation of the product can be conducted using magnetic avidin or streptavidin beads as shown in FIG. 7. In this case, magnetic streptavidin beads (MPG) were used to purify telomerase-specific biotin-labeled product. The 5'-biotinylated telomerase primer was used in the telomerase reaction. Detection by 32P label indicates that 100% of the signal is recovered. Without primer, no free label is bound to the beads.

Figure 9:
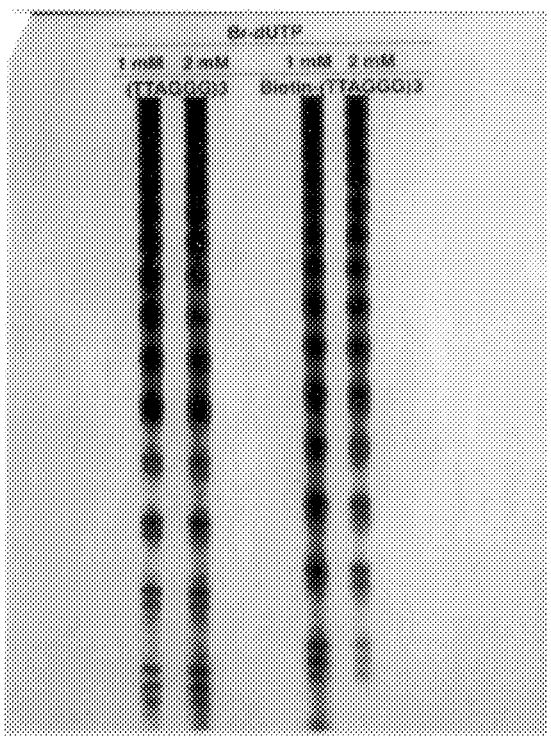
FIG. 9: Biotin-Primer Extension by Telomerase using BrdUTP as a Substrate. A biotinylated primer was extended by telomerase using BrdUTP as a substrate. Primer concentrations BrdUTP concentrations are listed for the reactions containing the indicated primers. The exponent "3" indicates three copies of the repeat are present in the primer.

The inventors also have determined, again surprisingly, that telomerases can incorporate modified nucleotides, such as bromodeoxyuridine triphosphate (BrdUTP), into the telomerase product, as shown in FIG. 8. The telomerase reaction was performed with (+) and without (−) BrdUTP to show that telomerase can utilize the BrdUTP as a substrate. The presence of the label allows for various rapid and automated methods for detecting the telomerase product. This offers a significant advantage over the complications involved with handling radioactive labels. The presence of a biotin molecule on the primer does not adversely affect the use of BrdUTP by telomerase, as shown in FIG. 9.

REFERENCES

The following references, to the extent that they provide exemplary procedural or other details supplementary to those set forth herein, are specifically incorporated herein by reference:

U.S. Pat. No. 4,683,195
U.S. Pat. No. 4,683,202
U.S. Pat. No. 4,800,159
U.S. Pat. No. 4,883,750
GB Application No. 2 202 328.
PCT Application No. PCT/US87/00880.
PCT Application No. PCT/US89/01025.
Chadeneau et al., *Cancer Res.,* 55:2533–2536, 1995.
Counter et al., *Proc. Nat'l Acad. Sci. USA,* 91:2900–2904, 1994.
Davey et al., European Patent Application Publication No. 329,822.
Frohman, In: *PCR Protocols: A Guide to Methods and Applications,* Academic Press, N.Y., 1990.
Hiyama et al., *Nature Medicine,* 1:249–255, 1995.
Hiyama et al., *J. Nat'l Cancer Inst.,* 87:895–902, 1995.
Innis et al., In: *PCR Protocols,* Academic Press, Inc., San Diego Calif., 1990.
Kim et al., *Science,* 266:2011–2015, 1994.
Maniatis et al., *Molecular Cloning,* Cold Spring Harbor Laboratory, Cold Spring Harbor, N.Y., 1982.
Miller et al., PCT Application WO 89/06700.
Morin, *Cell,* 59:521–529, 1989.
Ohara et al., *Proc. Nat'l Acad. Sci. U.S.A.,* 86:5673–5677, 1989.
Rhyu, *J. Nat'l Cancer Inst.,* 87:884–894, 1995.
Walker et al., *Proc. Nat'l Acad. Sci. (U.S.A.),* 89:392–396, 1992.

What is claimed is:

1. A method for detecting telomerase activity in a sample comprising the steps of:

(i) obtaining said sample;

(ii) contacting said sample with a telomerase primer and dNTPs under conditions permitting formation of a telomerase product;

(iii) contacting the telomerase product of step (ii) with a first oligonucleotide and a second oligonucleotide under conditions permitting hybridization, wherein said first and said second oligonucleotides hybridize to said telomerase product such that no single-stranded region intervenes between said first and said second oligonucleotides to form a hybridized product;

(iv) contacting the hybridized product and oligonucleotides with a ligase; and (v) detecting the ligated form of said first and said second oligonucleotides.

2. The method of claim 1, wherein steps (iii) and (iv) are repeated at least once prior to step (v).

3. The method of claim 2, wherein said ligase is a thermal-resistant ligase.

4. The method of claim 2, wherein said ligated form is amplified by a ligase chain reaction.

5. The method of claim 1, wherein said detecting further comprises electrophoretic separation of said ligated form.

6. The method of claim 1, wherein at least one of said first and said second oligonucleotides contains a detectable label.

7. The method of claim 6, wherein said label is selected from the group consisting of a radiolabel, a fluorescent label, a chemiluminescent label and a colorimetric label.

8. The method of claim 1, wherein said first oligonucleotide further comprises a first unique sequence attached to its 5'-end and said second oligonucleotide comprises a second unique sequence attached to its 3'-end.

9. The method of claim 8, wherein said detecting further comprises contacting said ligated form with a polymerase, a primer complementary to said second unique sequence and a primer complementary to said first unique sequence, performing sequence specific amplification and identifying the amplification product.

10. The method of claim 9, wherein said detecting further comprises electrophoretic separation of said amplification product.

11. The method of claim 9, wherein said amplification product contains a detectable label.

12. The method of claim 11, wherein said label is selected from the group consisting of a radiolabel, a fluorescent label, a chemiluminescent label and a colorimetric label.

13. The method of claim 1, wherein said sample is tumor tissue.

14. The method of claim 13, wherein said tumor tissue is selected from the group consisting of carcinomas of the breast, colon, esophagus, kidney, liver, lung, ovaries, prostate, stomach, uterus, pancreas and head and neck, sarcomas of bone and muscle, leukemias, myelomas, lymphomas, neuroblastomas, astrocytomas, gliomas, glioblastomas, retinoblastomas and melanomas.

15. The method of claim 13, further comprising the steps of:

(vi) quantifying the telomerase activity of said sample;

(vii) comparing the telomerase activity level with activity levels from normal and tumor sample standards; and (viii) making a prognostic evaluation or clinical decision regarding the patient from which said tumor tissue was obtained.

16. The method of claim 1, wherein either said first or said second oligonucleotide is attached to a support, at least the unattached oligonucleotide contains a detectable label and said detecting comprises identifying said label bound to said support.

17. The method of claim 16, wherein said attachment is effected by biotin/avidin.

18. The method of claim 16, wherein said label is a radiolabel, a fluorescent label, a chemiluminescent label and a colorimetric label.

19. The method of claim 18, wherein said label is a fluorescent label and the linked oligonucleotide is labeled with a distinct fluorescent label such that the fluorescence of one label induces or quenches the fluorescence of the other label.

20. The method of claim 18, wherein said label is a β-emitting radiolabel and the support contains a scintillant.

21. The method of claim 20, wherein said support is a bead.

22. A method for detecting telomerase activity in a sample comprising the steps of:

(i) obtaining said sample;

(ii) contacting said sample with a telomerase primer and dNTPs, wherein said dNTPs include BrdUTP or hapten-labeled nucleotides; and (iii) determining the incorporation of BrdU or hapten-labeled nucleotides into a telomerase product of step (ii).

23. The method of claim 22, wherein said determining comprises detecting BrdU covalently linked to said telomerase primer.

24. The method of claim 23, wherein the telomerase primer is attached to a support and said detecting comprises identifying BrdU linked to said support.

25. The method of claim 24, wherein said identifying comprises contacting said support with a first antibody that binds BrdU in a single-stranded polynucleotide.

26. The method of claim 25, wherein said first antibody contains a detectable label selected from the group consisting of a radiolabel, a chemiluminescent label, a fluorescent label and a colorimetric label.

27. The method of claim 25, further comprising the step of contacting said first antibody-bound support with a secondary antibody that is immunologically reactive with said first antibody, wherein said secondary antibody contains a label selected from the group consisting of a radiolabel, a chemiluminescent label, a fluorescent label and a colorimetric label.

28. The method of claim 25, wherein said first antibody is labeled with biotin or a hapten.

29. The method of claim 28, further comprising the step of contacting said first antibody-bound support with a second antibody that is immunologically reactive with said first antibody, or contacting said first antibody-bound support with avidin or a hapten-binding protein, wherein said second antibody, said avidin or said hapten-binding protein contains (i) a label selected from the group consisting of a radiolabel, a chemiluminescent label, a fluorescent label and a colorimetric label or (ii) a hapten.

30. A method for determining telomere length comprising the steps of:
   (i) providing a genomic DNA;
   (ii) contacting said genomic DNA with a plurality of oligonucleotides, under conditions permitting hybridization thereof, wherein said oligonucleotides hybridize to telomeric DNA such that no single-stranded regions intervenes between said hybridized oligonucleotides;
   (iii) contacting the hybridized telomeric DNA and oligonucleotides with a ligase; and
   (iv) determining the length of the ligated form of said oligonucleotides.

31. A method for obtaining a substance having telomerase-inhibiting activity comprising the steps of:
   (i) providing a telomerase preparation;
   (ii) contacting said telomerase preparation with a telomerase primer and dNTPs in the presence of said substance to form a telomerase product;
   (iii) contacting said telomerase product of step (ii) with a first oligonucleotide and a second oligonucleotide under conditions permitting hybridization, wherein said first and said second oligonucleotides hybridize to said telomerase product such that no single-stranded region intervenes between said first and said second oligonucleotides to form a hybridized product;
   (iv) contacting the hybridized product and oligonucleotides with a ligase;
   (v) detecting the ligated form of said first and said second oligonucleotides;
   (vi) comparing the amount of telomerase product of step (iii) with the amount of telomerase product synthesized in the absence of said substance; and
   (vii) obtaining said substance.

32. A method for obtaining a substance having telomerase-inhibiting activity comprising the steps of:
   (i) providing a telomerase preparation;
   (ii) contacting said sample with a telomerase primer and dNTPs, wherein said dNTPs include BrdU or hapten-labeled nucleotides and one or more candidate inhibitor substances to form a telomerase product;
   (iii) determining the incorporation of BrdU or hapten-labeled nucleotides into the telomerase product of step (ii);
   (iv) comparing the amount of telomerase product of step (ii) with the amount of telomerase product synthesized in the absence of each of said candidate inhibitor substances; and
   (v) obtaining said candidate inhibitor substance or substances.

33. The method of claim 32, wherein said dNTPs include BrdUTP.

34. The method of claim 33, wherein said dNTPs include hapten-labeled nucleotides.

35. A method for diagnosing cancer in a subject comprising the steps of:
   (i) obtaining a tissue sample from said subject;
   (ii) contacting said tissue sample with a telomerase primer and dNTPs to form a mixture;
   (iii) contacting the mixture of part (ii) with a first oligonucleotide and a second oligonucleotide under conditions permitting hybridization, wherein said first and said second oligonucleotides hybridize to a telomerase product such that no single-stranded region intervenes between said first and said second oligonucleotides;
   (iv) contacting the mixture of part (iii) with a ligase; and
   (v) determining if a ligated form of said first and said second oligonucleotides is present,
whereby the presence of a ligated form of said first and said second oligonucleotides is indicative of cancer.

36. The method of claim 35, further comprising determining if said a telomerase activity is processive or nonprocessive.

37. A method for determining the processivity of a telomerase comprising the steps of:
   (i) obtaining a sample;
   (ii) contacting separate portions of said sample with
      (a) a single repeat telomerase primer and dNTPs' and
      (b) a two-repeat telomerase primer and dNTP's;
   (iii) determining the presence or absence of telomerase extension products in each of said portions,
whereby the presence of telomerase extension products in both the portions indicates processive telomerase activity, and whereby the presence of telomerase extension products in only the two-repeat primed portion indicates non-processive telomerase activity.

38. The method of claim 37, wherein said determining comprises:
   (a) contacting said telomerase product with a first oligonucleotide and a second oligonucleotide under conditions permitting hybridization, wherein said first and said second oligonucleotides hybridize to said telomerase product such that no single-stranded region intervenes between said first and said second oligonucleotides to form a hybridized product
   (b) contacting the hybridized product and ligonucleotides of step (a) with a ligase; and
   (c) determining if a ligated form of said first and said second oligonucleotides is present in each of said single and said two-repeat primed portions.

39. The method of claim 37, wherein detection of a telomerase product in both in both the single and two-repeat primed portions indicates a processive telomerase and detection of telomerase activity in only the two-repeat primed portion indicates a non-processive telomerase.

40. A method for determining processivity of a telomerase comprising the steps of:

(i) obtaining a sample;

(ii) contacting separate portions of said sample with
(a) a telomerase primer not ending in TTAG and dNTPs; and
(b) a telomerase primer ending in TTAG and dNTPs; and (iii) determining the presence or absence of telomerase extensions products in said portions, whereby the presence of telomerase extension products in the portion comprising the TTAG telomerase primer indicates processive telomerase activity, and whereby the presence of telomerase extension products in the portion comprising the telomerase primer not ending in TTAG indicates total telomerase activity.

41. The method of claim 40, wherein said determining comprises:

(a) contacting said telomerase product with a first oligonucleotide and a second oligonucleotide under conditions permitting hybridization, wherein said first and said second oligonucleotides hybridize to said telomerase products such that no single-stranded region intervenes between said first and said second oligonucleotides to form hybridized products;

(b) contacting the hybridized products and oligonucleotides with a ligase; and (c) determining if a ligated form of said first and said second oligonucleotides is present in each of said TTAG primed and non-TTAG primed portions.

42. The method of claim 40, wherein detection of a telomerase product with said TTAGGG primer indicates processive and non-processive telomerase activity and detection of telomerase products with only the TTAG primer indicates a processive telomerase activity.

* * * * *

UNITED STATES PATENT AND TRADEMARK OFFICE
CERTIFICATE OF CORRECTION

PATENT NO. : 5,856,096
DATED : January 5, 1999
INVENTOR(S) : Windle et al.

It is certified that error appears in the above-identified patent and that said Letters Patent is hereby corrected as shown below:

On the title page, item [22], line 1, delete "Sep. 21, 1995", and insert the following therefor: -- Sep. 20, 1995 --.

In claim 39, column 26, line 62, delete "in both in both", and insert the following therefor: -- in both --.

Signed and Sealed this

Sixth Day of July, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TTAGGGTTAG GG                                          1 2

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CCCTAACCCT AA                                          1 2

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTAGGGTTAG GGTTAGGGTT AGGG                         2 4

( 2 ) INFORMATION FOR SEQ ID NO:4:

( i ) SEQUENCE CHARACTERISTICS:
        ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:4:

CCCTAACCCT AACCC 15

(2) INFORMATION FOR SEQ ID NO:5:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:5:

CCCTAACCCT AA 12

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:6:

CCCTAACCCT AACCCTAACC CTAACCC 27

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:7:

TTAGGGTTAG GGTTAGGG 18

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: double
(D) TOPOLOGY: linear (xi) SEQUENCE DESCRIPTION: SEQ ID NO:8:

TTAGGGTTAG GGTTAGGG 18

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: double
(D) TOPOLOGY: linear (xi) SEQUENCE DESCRIPTION: SEQ ID NO:9:

CCCTAACCCT AACCCTAA 18

(2) INFORMATION FOR SEQ ID NO:10:

(i) SEQUENCE CHARACTERISTICS:
(A) LENGTH: 10 base pairs
(B) TYPE: nucleic acid
(C) STRANDEDNESS: single ( D ) TOPOLOGY: linear ( x i ) SEQUENCE DESCRIPTION: SEQ ID NO:10:

TTAGGGTTAG 10

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTTAGGGTTA G 11

( 2 ) INFORMATION FOR SEQ ID NO:12:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CUAACCCUAA C 11

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTTAGGGTTA GGGTTAG 17

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCCTAACCCT AATGTACAAG ACTAGTGTCA 30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CGGCGTACAC GGAGCTGACC CTAACCCTAA 30

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:16:

TGACACTAGT CTTGTACA                     18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CGGCGTACAC GGAGCTGA                     18